(12) United States Patent
Warner et al.

(10) Patent No.: US 12,076,151 B2
(45) Date of Patent: Sep. 3, 2024

(54) CUSTOMIZABLE INTERFACE SYSTEM FOR INVASIVE CARDIOLOGY AND ELECTROPHYSIOLOGY

(71) Applicant: General Electric Company, Schenectady, NY (US)

(72) Inventors: Adrian F. Warner, Delafield, WI (US); Daniel R. Schneidewend, Menomonee Falls, WI (US); Timothy P. Stiemke, West Bend, WI (US); Rodger F. Schmit, West Bend, WI (US); Daniel P. Mabini, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 228 days.

(21) Appl. No.: 16/023,299

(22) Filed: Jun. 29, 2018

(65) Prior Publication Data

US 2020/0000358 A1    Jan. 2, 2020

(51) Int. Cl.
*A61B 18/00* (2006.01)
*A61B 5/00* (2006.01)
(Continued)

(52) U.S. Cl.
CPC ............... *A61B 5/287* (2021.01); *A61B 5/30* (2021.01); *A61B 5/6852* (2013.01);
(Continued)

(58) Field of Classification Search
CPC ............... A61B 5/0422; A61B 5/0428; A61B 5/6852; A61B 5/7217; A61B 5/6547;
(Continued)

(56) References Cited

U.S. PATENT DOCUMENTS 5,997,528 A * 12/1999 Bisch .................. A61F 9/00736
606/1
6,088,021 A    7/2000 Yong
(Continued)

FOREIGN PATENT DOCUMENTS

CN        105120765 A    12/2015
JP        2007521048 A     8/2007
(Continued)

OTHER PUBLICATIONS

JP application 2019-118087 filed Jun. 26, 2019—Office Action dated Nov. 2, 2021; 7 pages.
(Continued)

*Primary Examiner* — Joanne M Rodden
*Assistant Examiner* — Rachel A. Vierra
(74) *Attorney, Agent, or Firm* — Andrus Intellectual Property Law, LLP (57) ABSTRACT

A physiological data acquisition system includes at least one interface module and a base unit configured to communicatively connect to the at least one interface module to receive the physiological signals recorded by a catheter. Each interface module is formed by mating at least a first one of the two or more different personality modules to a dock. The dock has a multi-modal connection port configured to directly connect to a dock connector of any one of the two or more different personality modules so as to receive physiological signals therefrom. The first personality module includes a first catheter connector configured to receive a connection end of the catheter so as to receive physiological signals therefrom, and a first dock connector configured to connect to the multi-modal connection port of the dock so as to provide the physiological signals thereto.

17 Claims, 8 Drawing Sheets

(51) Int. Cl.
*A61B 5/287* (2021.01)
*A61B 5/30* (2021.01)
*A61B 18/14* (2006.01)
*A61B 5/304* (2021.01)

(52) U.S. Cl.
CPC .......... *A61B 18/1492* (2013.01); *A61B 5/304* (2021.01); *A61B 5/7217* (2013.01); *A61B 5/742* (2013.01); *A61B 2018/00577* (2013.01); *A61B 2018/00839* (2013.01); *A61B 2560/0443* (2013.01); *A61B 2560/045* (2013.01); *A61B 2560/0456* (2013.01); *A61B 2562/08* (2013.01)

(58) Field of Classification Search
CPC . A61B 5/6846; A61B 5/0205; A61B 18/1492; A61B 2018/00267; A61B 2018/00351; A61B 2018/00577; A61B 2018/00839; A61B 2018/00172; A61B 2560/045; A61B 2562/08; A61B 90/90–98; H01R 13/64; A61N 1/3752
See application file for complete search history.

(56) References Cited

U.S. PATENT DOCUMENTS

| | | | |
|---|---|---|---|
| 7,873,409 | B2 | 1/2011 | Schneidewend et al. |
| 9,522,048 | B1 | 12/2016 | Schmit et al. |
| 10,881,314 | B2 | 1/2021 | Muuranto |
| 2004/0024395 | A1* | 2/2004 | Ellman ............... A61B 18/12 606/37 |
| 2007/0016034 | A1* | 1/2007 | Donaldson ........... A61B 8/0833 600/437 |
| 2007/0276272 | A1* | 11/2007 | Schneidewend ......... A61B 5/30 600/509 |
| 2008/0255504 | A1* | 10/2008 | Nekich ................ A61B 5/304 604/95.01 |
| 2010/0204569 | A1* | 8/2010 | Burnside .............. A61B 5/042 600/424 |
| 2011/0144806 | A1 | 6/2011 | Sandhu et al. |
| 2012/0071744 | A1* | 3/2012 | Euliano, II ........... A61B 5/033 600/382 |
| 2014/0275844 | A1* | 9/2014 | Hoseit .................... A61B 8/12 600/407 |
| 2016/0135878 | A1 | 5/2016 | Warner et al. |
| 2016/0184025 | A1 | 6/2016 | Warner et al. |
| 2016/0188827 | A1 | 6/2016 | Warner et al. |
| 2017/0095289 | A1 | 4/2017 | Warner et al. |
| 2018/0317826 | A1* | 11/2018 | Muhsin .............. A61B 5/14552 |

FOREIGN PATENT DOCUMENTS

| | | | |
|---|---|---|---|
| JP | 2018504192 A | 2/2018 | |
| WO | WO-2015000500 A1 * | 1/2015 | ............ A61B 5/287 |

OTHER PUBLICATIONS

PCT application WO/2005/055822—Abstract; Espacenet search results Feb. 1, 2022; 1 page.
CN application 201910579736.1 filed Jun. 28, 2019—Office Action dated Dec. 3, 2021; 9 pages.

* cited by examiner

CUSTOMIZABLE INTERFACE SYSTEM FOR INVASIVE CARDIOLOGY AND ELECTROPHYSIOLOGY

BACKGROUND

The present disclosure generally relates to signal acquisition systems, and more particularly to interface systems for physiological data acquisition in the fields of invasive cardiology and electrophysiology.

Catheters are used in an increasing number of medical procedures to evaluate various conditions of the patient with which the catheter is utilized. While many different numbers and/or configurations of catheters can be utilized for a particular procedure, for each procedure all of the catheters in use must be properly connected to the recording or mapping device such that the signals received from or sent to a particular catheter are correctly identified and displayed by the recording or mapping device.

The catheters are connected to an input module, such as a pin box or other suitable connector, used with the recording or mapping device. Each catheter is connected to a specific location or port on the catheter module that corresponds to a particular location in the patient at which the catheter is positioned during the performance of the procedure. This location or port is additionally associated with a particular signal display on the screen of the recording or mapping device, such that during the procedure signals received from or sent to the catheter at that port are illustrated on the display in the field corresponding to that port.

During initial set up and connection of the catheters to perform a procedure, on many occasions one or more catheters can be inadvertently connected to the incorrect ports, such that incorrect signals are represented on the display viewed by the clinician. This results at least in requiring the clinician or other individual to check the catheter connections for the incorrect connection, but can also result in confusion during the diagnostic process. Further, in a situation where only a single catheter is used and the catheter is incorrectly placed in the pin box, the determination of the faulty electrode, bad lead, and/or unintended disconnect is relatively straightforward with basic physiological instrumentation. However, this challenge increases exponentially with complex patient studies such as performed in cardiac electrophysiology where catheter/lead sets of up to 256+ individual 2 mm pin connections are possible, such as when using complex mapping catheters, for example, that can include seven or more separate input modules, connectors or pin boxes, each with up to thirty-two separate ports thereon. In these situations, the incorrect placement of a catheter that is functioning incorrectly can result in significant waste of clinician time, frustration in obtaining the correct signals on the display, and possibly confusion in diagnosis of the patients physiological signals.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a physiological data acquisition system includes at least one interface module and a base unit configured to communicatively connect to the at least one interface module to receive the physiological signals recorded by a catheter. Each interface module is formed by mating at least a first one of the two or more different personality modules to a dock. The dock has a multi-modal connection port configured to directly connect to a dock connector of any one of the two or more different personality modules so as to receive physiological signals therefrom. The first personality module includes a first catheter connector configured to receive a connection end of the catheter so as to receive physiological signals there from, and a first dock connector configured to connect to the multi-modal connection port of the dock so as to provide the physiological signals thereto.

In another embodiment, a personality module configured to mate with a dock so as to form an interface module, wherein the personality module includes a personality module housing, a catheter connector on the personality module housing and configured to receive a connection end of a catheter so as to receive physiological signals therefrom, and a dock connector on the personality module housing configured to directly connect to a multi-modal connection port of the dock so as to provide the physiological signals thereto. The personality module housing is configured to engage a dock housing of the dock so as to removably mate with the dock to form the interface module.

In still another embodiment, a physiological data acquisition system includes a base unit configured to communicatively connect to a first interface module and a second interface module to receive the physiological signals therefrom. The first interface module has a first dock configured to mate with at least one personality module. The first dock has a first dock housing and at least a first multi-modal connection port on the first dock housing configured to connect to the personality module so as to receive physiological signals therefrom. The first personality module has a first personality module housing, a first catheter connector on the first personality module housing, wherein the first catheter connector is configured to receive a connection end of a first catheter type so as to receive physiological signals therefrom, and a first dock connector on the first personality module housing, wherein the first dock connector is configured to connect to the first multi-modal connection port of the first dock so as to provide the physiological signals thereto. The first dock housing and the first personality module housing are correspondingly shaped such that they mate together to form the first interface module. The system further includes a second interface module having a second dock configured to mate with at least one personality module. The second dock has a second dock housing and a second multi-modal connection port on the second dock housing configured to connect to the personality module so as to receive physiological signals therefrom. The second dock is connected to at least a second personality module having a second personality module housing, a second catheter connector on the second personality module housing, the second catheter connector configured to receive a connection end of a second catheter type so as to receive physiological signals therefrom, and a second dock connector on the second personality module housing, wherein the second dock connector is configured to connect to the second multi-modal connection port of the second dock so as to provide the physiological signals thereto. The second dock housing and the second personality module housing are correspondingly shaped such that they mate together to form the second interface module.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The present inventors have recognized a need for an improved data acquisition interface system for use in invasive cardiac procedures and in hemodynamic and electrophysiology applications, such as for cardiac catheterization procedures and in electrophysiology labs. The connection of catheters to monitoring devices has been a long standing challenge in the fields of invasive cardiology and electrophysiology. In most currently available systems, connection of catheters to interface modules is a laborious, cumbersome, and error prone. Most catheters have "ponytail" connectors comprised of several 2 mm pins at the end of the catheter electrode wires, where the 2 mm pins must be individually connected to ports on an interface module. On a catheter having 10 electrodes, for example, the ponytail connector includes 10 electrode wires each terminating at a 2 mm pin that must be connected at a location on a grid of pin receivers on the interface module. Standard interface module includes grids of 32 pin receivers, or more. Furthermore, multiple catheters, each having a dedicated interface module, may be utilized in any given procedure. Accordingly, pins are easily misconnected by connecting one more pins to the wrong pin receivers or pairing the wrong electrodes at the catheter input module relative to the configuration programmed into the EP recorder or mapping system. The problem is exacerbated by the sheer number of connections that must be made in any given procedure, which can reach 256+ connections, with certain procedures demanding an even greater number of connections.

Many attempts have been made to simplify the connection process by providing single connectors that organize the electrode connections in a pre-set way and allow easy connection and disconnection of the catheter via a single connector. One example of such a single connector is the Carto 3 Patient Interface Unit from Biosense Webster. However, the relevant industries have never developed or agreed on any standard for connection. Furthermore, differing catheters often have differing needs that can be hard to resolve with a fixed catheter input module. For example, the Advisor™ Grid Catheter by Abbot can be difficult to connect and map across a conventional 32 input CIM.

Thus, while certain catheter suppliers have developed or attempted to develop catheters with a unitary connector, manufacturers have developed their own proprietary connection devices and/or connection methods, such as through proprietary connectors or via proprietary pin out wiring. Such catheters with proprietary connectors require proprietary receivers and thus proprietary interface modules. Given that multiple different types of catheters from multiple different suppliers may be utilized in a single procedure, and that medical facilities may utilize different types of catheters from different manufacturers, utilization of separate proprietary monitoring systems becomes unwieldy, increasing patient exam set-up times. This has lead to the persistent use of the ponytail connectors (also known as "transition connectors"), which have become the generic connectors of choice. Thus, despite the fact that ponytail connectors are cumbersome and potentially error-prone, their use has continued to be prevalent.

In view of these long standing and persistent problems, and based on their extensive experimentation and research in the relevant field, the inventors have developed the disclosed customizable data acquisition interface system having modularized interface modules that can be assembled and customized for particular procedures, applications, and devices. Each interface module includes a dock portion that mates with any of multiple different connection modules—i.e., "personality modules"—configured to receive one or more catheters or physiological recording sensors. Each dock has at least one multi-modal connection port configured to directly connect with a corresponding connector of any two or more different types of personality modules to form a customized interface module. Thus, the dock provides a generic connection location for many different types of data acquisition devices, including many different catheter types and physiological monitor types which may each have a corresponding personality module. The personality modules can be individually selected and organized to create an interface module for a particular procedure or a particular clinician.

The personality modules may be passive—just configured to conduct physiological signals received from the catheter to the dock—or active, including analog and/or digital signal processing components. In certain embodiments, the dock may be configured to interchangeably connect with any number of different active and passive personality modules. Furthermore, the dock may be configured to connect to multiple personality modules at once, which may be a combination of active and passive personality modules.

The personality modules may be configured to connect to particular types of catheters, such as having reception ports for proprietary catheter connectors. Moreover, in addition to a multitude of different available catheter personality modules, the system may include personality modules configured to receive and process physiological recording inputs, such as from electrocardiograph (ECG) surface electrodes, invasive blood pressure sensors, electroencephalograph (EEG) electrodes, $SpO_2$ sensors, etc. Thus, further customization of interface modules are provided which allow all the different types of data acquisition devices utilized in a wide range of procedures to be easily connected into a single data acquisition system.

The personality module may include signal processing hardware and/or software configured to process the type of signal from the proprietary catheter, or from any particular type of catheter device. Likewise, the personality module may include signal processing hardware and/or software configured to process the type of physiological signals recorded by any type of physiological recording electrode or sensor, such as filtering and amplifying EEG signals, invasive blood pressure signals, ECG signals, SpO$_2$ signals, etc.

The dock may be configured to receive analog physiological signals, digitized physiological data, or both. Additionally, the dock may comprise a computing system configured to identify the type of personality module connected thereto and provide specialized processing functionality based thereon. For example, the dock may be configured to provide specialized signal processing functionality based on the type of personality module mated to the dock.

Accordingly, multiple different personality modules configured to connect to multiple different proprietary catheters and or physiological sensors may be mated with a single dock, creating an interface module that is customized for the exact catheters and patient monitoring functions that will be used in a particular procedure. This provides a compact and organized data acquisition system that is less cumbersome to manage than existing systems and allows multiple different types of proprietary catheter connections and physiological recording connections to be easily provided in an organized way, and thus significantly reducing the chance of error due to misconnection.

Figure 1:
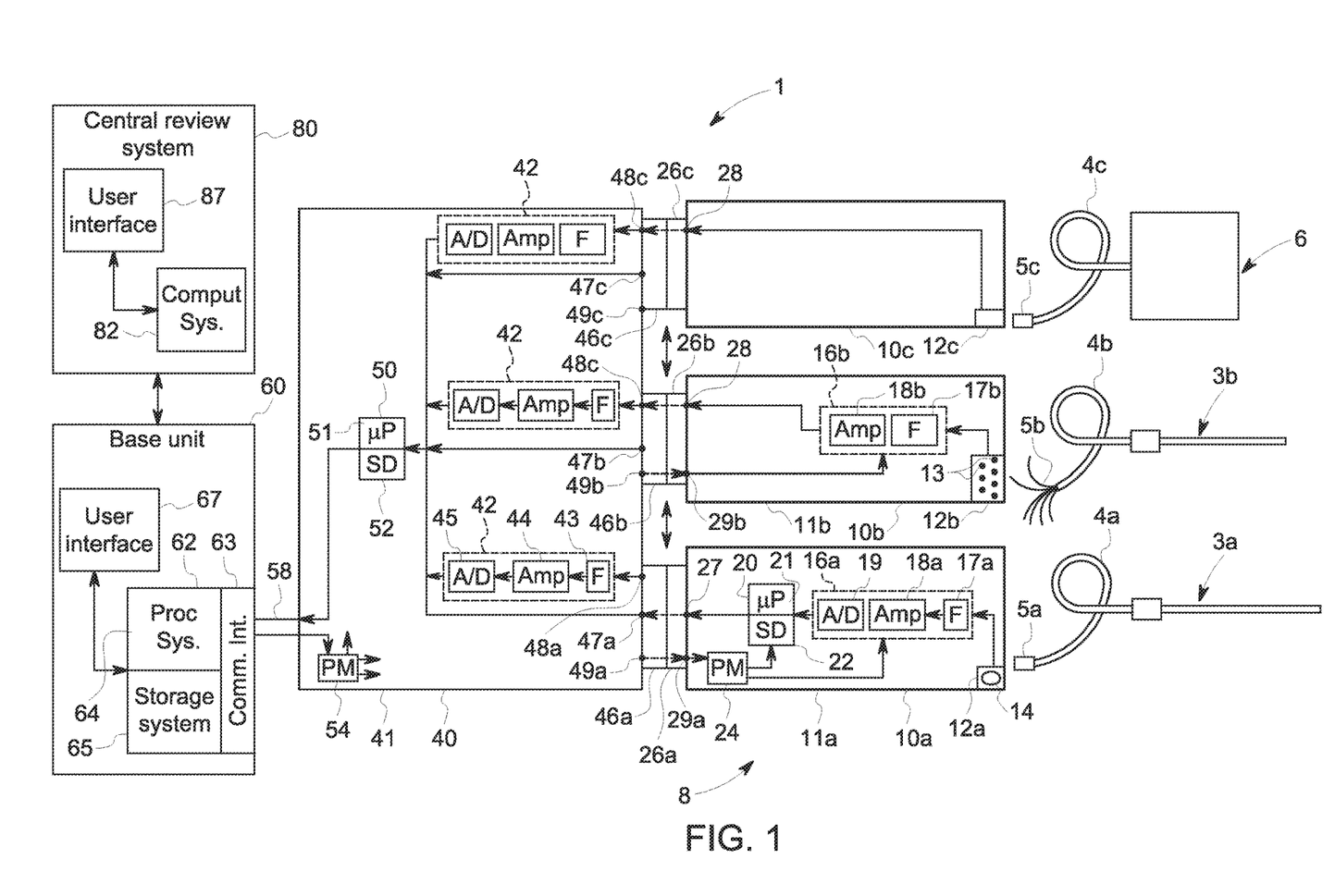
FIG. 1 depicts one embodiment of an exemplary customizable interface system for physiological data acquisition according to the present disclosure.

FIG. 1 depicts one exemplary embodiment of a customizable interface system 1 for physiological data acquisition having an interface module 8 according to the present disclosure. The interface module 8 includes a dock 40 connected to multiple different personality modules 10. In the depicted embodiment, the dock 40 has three multi-modal connection ports 46a-46c, and thus is configured to mate with three personality modules 10a-10c. However, other embodiments of the dock 40 may be configured to mate with any number of one or more personality modules 10.

In the depicted embodiment, the multi-modal connection port 46 has both digital connections 47 and analog connections 48, and thus the multi-modal connection port 46 is configured to interchangeably connect with either an active personality module 10 providing digital physiological signals or a passive personality module 10 providing analog physiological signals. Each of the multi-modal connection ports 46a-46c is identical, and thus the personality modules 10a-10c are interchangeable and connect with any of the multi-modal connection ports 46. Accordingly, the dock 40 may be configured to process a digitized output of all physiological signals received at the dock 40 to the base unit 60.

In other embodiments, the dock 40 may be configured to receive only analog signals from personality modules 10 and be configured to only provide an analog output of physiological signals to the base unit 60, or to receive only digital signals from personality modules 10 and provide only digital output to the base unit 60. In still other embodiments, the dock 40 may be configured to selectively provide either one of analog or digital outputs to the base unit 60 depending on the type of signals being received from the personality modules 10.

The system 1 is configured to incorporate any number of different types of personality modules 10, which are interchangeable to mate with the dock 40. In the depicted example, a first personality module 10a has a first receiver 12a configured to receive a connection end 5a of a first catheter type 3a. The first catheter type 3a may be any type of catheter for any number of different types of procedures. For example, the first catheter type may be any one of various available types of catheter configurations, including but not limited to fixed curve catheter, a mapping catheter, or a steerable catheter, an ablation catheter (including any of a growing number of ablation catheter subtypes, such as radiofrequency, laser, and cryogenic), or a multi-array catheter (such as a basket catheter or a grid catheter), or any other multipolar electrode catheter configuration (e.g., any quadripolar, duodecapolar, or halo catheter) and/or any proprietary version thereof. Particular examples of popular catheters that fall into these broader catheter types include, but are in no way limited to, any of the Advisor™ family of catheters by Abbott, the Orion mapping catheter by Boston Scientific, and the Topera FIRMap balloon catheter by Abbott, any diagnostic catheter by Medtronic, just to name a few.

Each catheter 3a, 3b may have a cable 4 or other transmission means having connector end 5a, 5b that gets plugged into a receiver 12a, 12b. For example, the catheter connection end 5a may be a proprietary connector, and the receiver 12a may be a unitary catheter receiver 14 configured to receive that proprietary connector. In such embodiments, the personality module 10a may be a dedicated personality module configured to receive process the signals from that particular catheter type.

A second personality module may be provided having a different receiver 12, which may be configured to receive any of various types of catheters or may be configured to receive a connection end of a physiological recording sensor (such as a surface electrode). Accordingly, the personality module may be chosen based on the type of data acquisition device to be connected. In the example, the second personality module 10b is configured to connect to a catheter type 3b that has a connection end 5b that is a ponytail connector having 2 mm pins that get individually connected to the pin receivers 13. The second personality module 10b has receiver 12b that is a grid of 2 mm pin receivers 13. Various such personality modules 10b may be available providing different numbers of 2 mm pin receivers 13, such as grids comprising 6, 12, 18, 32, and 64 pin receivers 13 (as well as grids having any other number of receivers 13, which can be greater than 64 receivers). The second catheter type 3b may be any of various types of catheters, including the examples described above.

A third personality module 10c is also provided which is configured to connect to a physiological data acquisition device 6, which could be any device configured to acquire physiological data. For example, the physiological data acquisition device 6 could be another catheter, or could be physiological recording electrodes or other sensors configured to record physiological signals from the patient, such as surface EEG electrodes, surface ECG electrodes, invasive ECG electrodes (iECG), surface or invasive EMG electrodes, or invasive blood pressure sensors, respiration monitoring electrodes, temperature sensors, or any other sensor configured to sense a physiological parameter from the patient's body. In still other embodiments, the physiological data acquisition device 6 could be strain gauges, pressure sensors, temperature sensors, light sensors, refraction sensors, or any other sensor sensing a physical parameter. In such an embodiment, the personality module 10 may comprised signal processing hardware and/or software configured to filter, amplify, isolate, and otherwise process the physiological signals, and thus to provide some or all of the signal processing functions of a patient monitor.

As described above, the personality modules 10 may be either passive or active devices. Personality module 10c exemplifies a completely passive device that just provides connection between the analog output of the physiological data acquisition device 6 received at the catheter connection 12*c* to the dock 40. Specifically, the passive personality module 10*c* has a dock connector 26*c* configured to connect with the multi-modal connection port 46*c* of the dock 40. The dock connector 26*c* on the personality module 10*c* has one or more analog connections 28 that galvanically connect with one or more corresponding analog connections 48*c* at the third multi-modal connection port 46*c*.

In other embodiments, the personality module 10 may be an active personality module containing a signal processing unit 16. The signal processing unit may be configured with any of various analog or digital components, and may be configured to provide signal processing that is unique to the particular catheter 3 or other physiological data acquisition device 6 connected thereto. For example, the signal processing unit 16 may be configured to filter out certain frequencies or other known noise elements that may appear in signals from certain types of catheters. For instance, the signal processing unit 16 may have analog or digital components configured to filter out carrier frequencies commonly used for location tracking for non-location-tracking catheter types, or configured to reject artifacts caused by other equipment, such as pacemaker or ablation devices.

The signal processing unit 16 may contain only analog-domain components, or may contain a digitizer to convert the analog physiological signals to digital physiological data. In the depicted embodiment of FIG. 1, personality module 10*b* contains a signal processing unit 16*b* providing analog components, including a filter 17*b* and an amplifier 18*b* configured to amplify the filtered physiological signals. For example, the filter 17*b* may be any type of analog filter, such as a notch filter, a bandpass filter, a band reject filter, etc. For example, the filter 17*b* may be configured to selectively filter expected noise elements in physiological signals from the second catheter type 3*b*. The signal processing unit 16*b* provides the filtered and amplified physiological signals to the dock 40 through the analog connection(s) 28 in the dock connector 26*b* to the analog connection(s) 48 in the multi-modal connection port 46*b*.

Personality module 10*a* provides an example of an active personality module having a signal processing unit 16*a* having both analog and digital components. The signal processing unit 16*a* includes a filter 17*a*, an amplifier 18*a*, and an analog-to-digital (A/D) converter 19. Accordingly, the signal processing unit 16*a* outputs digital physiological data. In the depicted embodiment, the personality module 10*a* further includes a computing system 20 configured to further process the physiological data. For example, the computing system 20 may house software configured to perform specific signal processing routines based on the type of acquisition device that the personality module 10 is configured to connect to, which in this embodiment is the first catheter type 3*a*. The computing system 20 includes a processing system 21 having one more processors, and a storage system 22 including one or more storage devices.

The dock 40 may be configured to supply power to one or more the active personality modules 10 so as to power the processing. In certain embodiments, such as ablation catheters, power may also be provided through the personality module 10 to the catheter 3 or other physiological data acquisition device 6. In the depicted embodiment, power is provided through the multi-modal connection port 46 to the respective personality module 10. More specifically, power is provided from a power connection 49 to a respective power connection 29 in the dock connector 26. The power may be passively transmitted from the power connection 29 to the various elements within the personality module 10 requiring power. In other embodiments, the personality module may include a power management module 24 that manages and distributes power received from the dock 40. Personality module 10*a* exemplifies such an embodiment having a power management module 24. The power management module 24 may include, for example, a battery that stores energy received at the power connector 29 and distributes that power to the various powered elements of the personality module 10*a*, such as the computing system 20 and the signal processing unit 16. Such power management capabilities may be required for embodiments of personality modules 10 containing demanding or sensitive electrical components, or in embodiments where power is supplied to the catheter 3 or other physiological acquisition device. In still other embodiments, especially for active personality modules 10 providing digital physiological data outputs, the personality module 10 may contain a rechargeable battery that gets charged before use and connection to the dock 40, wherein the battery provides all the necessary power for the functions of the personality module 10.

As described above, each multi-modal connection port 46 on the dock 40 is configured to connect with a corresponding dock connector 26 on any of various different types of personality modules 10. The multi-modal connection port 46 may be configured in any manner known in the art for performing the functions described herein. The purpose of the multi-modal connection port is to receive physiological data or signals from the respective personality module 10, which in various embodiments may be analog or digital signals, or both. The multi-modal connection port 46 may also be configured to offer power transfer to a connected personality module 10 to power active modules as described above. In various embodiments, the power transfer may be provided through galvanic connections between the power connection(s) 49 in the multi-modal connection port 46 and the power connection(s) 29 in the dock connector 26. In other embodiments, power transfer may be provided through inductive or capacitive coupling between the respective power connection(s) 49, 29. Exemplary configurations for transferring the signals or data through the interface between the multi-modal connection port 46 and the dock connector 26 may be through physical, galvanic connection, radio frequency protocol, or by optimal data transfer. In one embodiment, galvanic connections are provided between the digital connection(s) 27 and analog connection(s) 28 in the dock connector 26 and the corresponding digital connection(s) 47 and analog connection(s) 48 in the multi-modal connection port 46. In one embodiment, the digital connections 27, 47 may each be a universal asynchronous receiver/transmitter (UART), and thus may include an integrated circuit to translate data between parallel and serial forms. The dock 40 may further include a power management module 54 that stores and/or provides power to the various elements within the dock 40, including the computing system 50 and/or the signal processing unit(s) 42 (connections not shown in FIG. 1 for visual clarity).

In certain embodiments, the multi-modal connection port 46 may be a dedicated analog or dedicated digital connection port, and in various embodiments the dock 40 may provide one or both types of dedicated connection ports. In embodiments where the multi-modal connection port 46 is a dedicated digital connection port, it may be configured as $I^2C$ or a serial peripheral interface (SPI). The data communication between the multi-modal connection port 46 and the dock connector 26 may alternatively be implemented using RF communication, such as Bluetooth, near field communication (NFC), ANT, or any other protocol suitable for short range communication. Due to the close proximity of the personality module 10 and the dock 40, the RF range can be quite short and the antenna can be optimized to utilize very little power and provide very local RP communication.

Figure 2A:
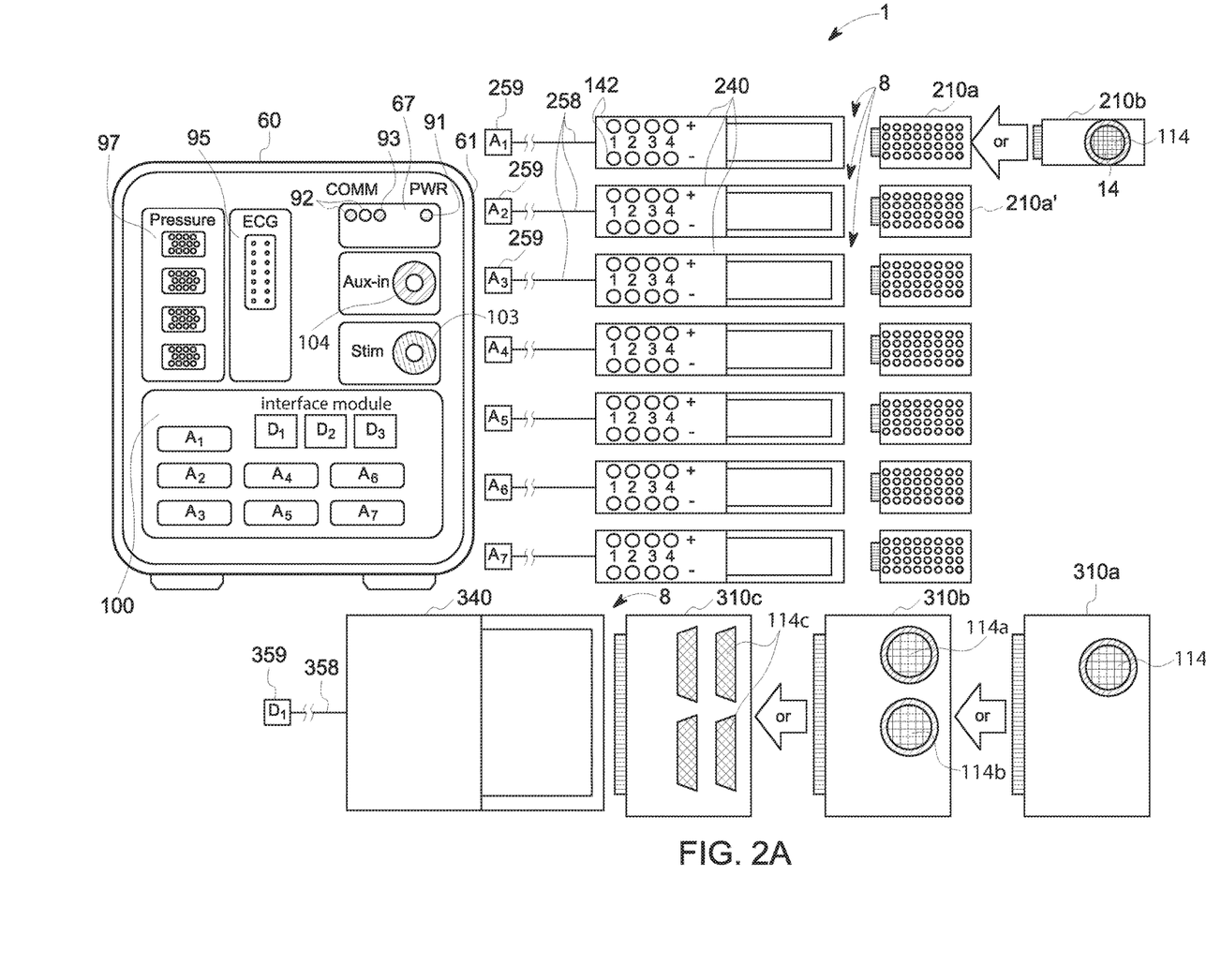
FIG. 2A depicts another embodiment of a customizable interface system for physiological data acquisition according to the present disclosure.

In various embodiments, each dock 40 may be dedicated analog docks or digital docks providing only analog or digital multi-modal connection ports 46. In other embodiments, docks 40 may have a mix of dedicated digital and dedicated analog multi-modal connection ports 46. In still other embodiments, such as that depicted in FIG. 1, the multi-modal connection port 46 may provide both analog and digital connections. FIG. 2 exemplifies an embodiment of the customizable interface system 1 having seven analog docks 240 and one digital dock 340. The seven analog docks 240 are each configured to connect to a corresponding analog receiver port $A_1$-$A_7$ on the base unit 60. An interface module connection area 100 on the housing 61 of the base unit 60 provides multiple dedicated analog connection receivers $A_1$-$A_7$ for connecting with dedicated analog docks 240. Specifically, each dock 240 may include transmission means being a transmission cable 258 terminating at a base connector 259 configured to galvanically connect with one of the analog receivers $A_1$-$A_7$ at the base unit 60.

Similarly, digital docks 340 may connect to digital receivers $D_1$-$D_3$ in the interface module section 100 of the base unit 60. The digital dock 340 may connect to the base unit 60 by any of various transmission means. For example, the transmission means for the digital communication may comprise a transmission cable 358 terminating at a base connection 359 configured to physically connect to a digital receiver $D_1$ and the base unit 60. In other embodiments, transmission means for the digital communication may be a wireless device configured to wirelessly communicate with the base unit 60. In such an embodiment, each of the digital dock 340 and the base 60 has a wireless transceiver configured to communicate, such as to transmit the physiological data from the digital dock 340 to be received at the corresponding wireless receiver $D_1$-$D_3$ at the base unit 60. Such wireless communication may be any of various wireless communication protocols, such as Bluetooth, Bluetooth low energy (BLE), ANT, and ZigBee. In other embodiments, the wireless digital receivers $D_1$-$D_3$ and the wireless transmitter in the digital dock 340 may be body area network (BAN) devices, such as medical body area network (MBAN) devices that operate on a wireless network of wearable, reportable physiological recording devices. In such an embodiment, the base unit 60 may be placed in proximity of the invasive cardiac or EP procedure, and the one or more digital docks 340 may be placed on or near the procedure table and physically connected to the catheters 3 or other peripheral data acquisition devices 6. In still other embodiments, the wireless communication may be by a longer range wireless protocol, such as a network operating on the wireless medical telemetry service (WMTS) spectrum or on a Wi-Fi compliant wireless local area network (WLAN).

Figure 2B:
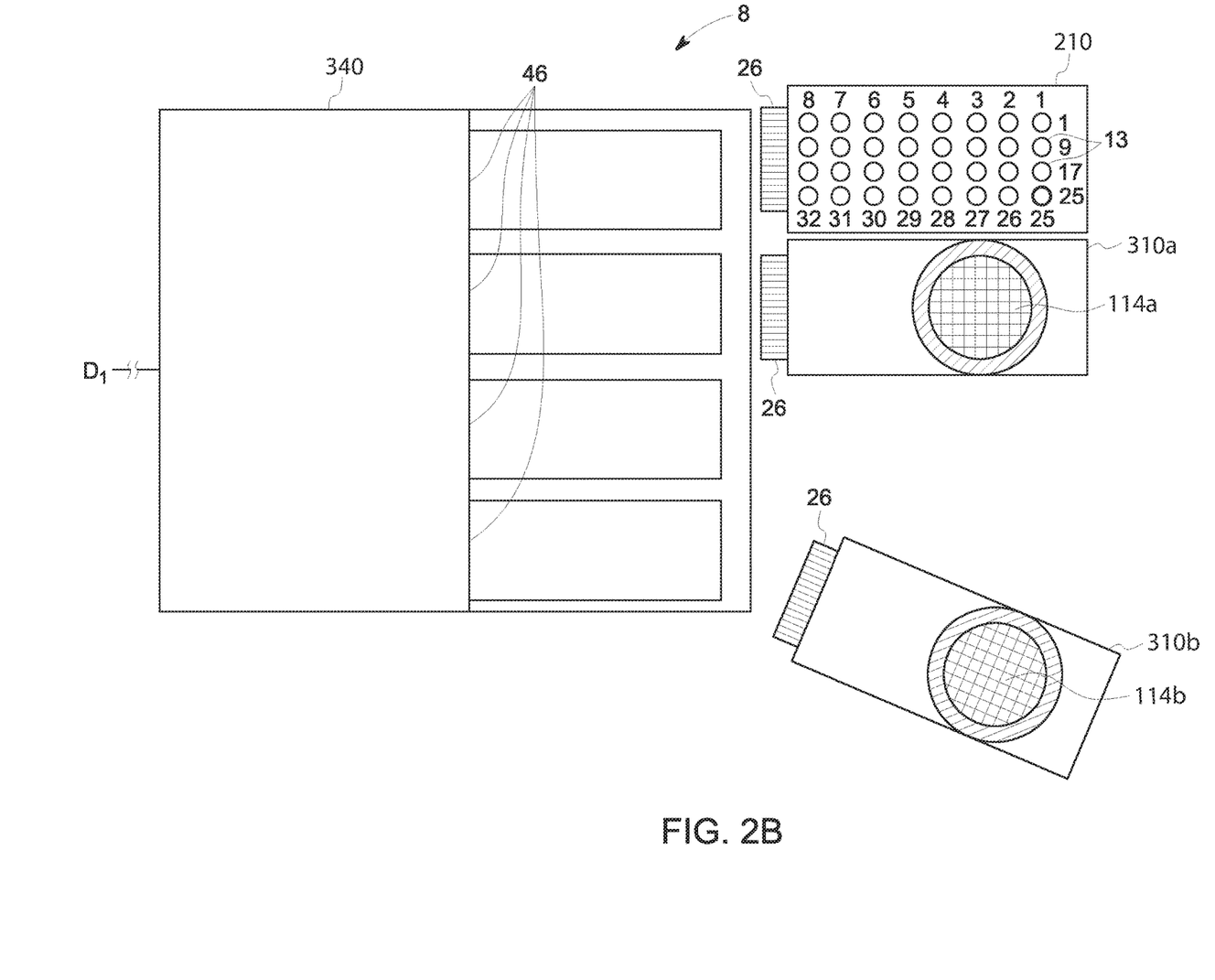
FIG. 2B depicts a dock configured to receive four personality modules to form an interface module comprising part of the customizable interface system of FIG. 2A.

With continued reference to FIGS. 2A and 2B, each of the docks 240, 340 are configured to receive one or more personality modules 210, 310 which define the function of the respective interface module 8. In the embodiment depicted in FIG. 2, each interface module 8 is comprised of only one personality module 10. In other embodiments, examples of which are shown and described herein, the interface module 8 may be comprised of multiple personality modules 10. Further, the system 1 may include multiple interface modules 8, each customized to particular data acquisition function according to their connected personality module(s) 10. In FIG. 2, the analog interface modules 8 each comprise an analog dock 240 configured to mate with any of the exemplary personality modules 210a, 210a', 210b. In this example, the analog personality modules 210a, 210a' are each configured with 2 mm pin receivers 13. The 2 mm pin receiver personality modules 210a, 210a' may be identical, or they may be different in that they may each be configured for different catheter applications and to perform different signal processing functions. The depicted example also includes an analog personality module 210b having a unitary receiver 114 for receiving a unitary catheter connection end 5. For example, the unitary receiver 114 may be a dedicated catheter receiver configured to connect to a particular catheter type (or two or more particular catheter types, similar to the interface module examples 310), such as one or more proprietary connectors by particular catheter manufacturers, standardized connectors for catheters performing a particular function, or general purpose catheters configured for different procedural workflows (mapping, ablation, pacing, etc.). For example, the personality module 210b could be configured to connect to any two or more of quadripolar catheters, decapolar catheters, split tip catheters, etc. These permutations would reflect typical user connection preferences such that the user can use the unitary receiver personality module in a similar manner to a 2 mm pin module in that multiple different catheters and catheter types can be connected thereto.

The digital dock 340 may be similarly configured to receive any of various personality modules 310a-310c, and may be configured to accept passive personality modules, active personality modules, or both. Referring also to FIG. 1, the dock 240 may be configured, for example, to receive both analog and digital signals. Where analog signals are received, the dock 340 may include a signal processing unit 42 configured to filter, amplify, and digitize the physiological signals in order to produce physiological data. Alternatively or additionally, the physiological signals received from the data acquisition device 3, 6 may be digitized in signal processing units 16 comprised within the personality modules 310a-310c and to provided the digitized physiological data to the dock 340.

In addition to the dock 340 being configured to receive multiple different personality modules 310, each personality module 310 may be configured to receive one or multiple connection ends 5 of catheters. In the example at FIG. 2, three different personality modules 310a-310c are connectable to the digital dock 340, each providing different catheter connection abilities. The first personality module 310a includes a first dedicated catheter receiver 114a configured to connect to a first catheter type 3a. The second personality module 310b has two different dedicated catheter receivers 114a, 114b, which are each configured to receive a different type of catheter. Personality module 310c has a third type of dedicated catheter receiver 114c, and is configured to receive four of the same catheter type. As will be understood by a person having ordinary skill in the art in light of this disclosure, the personality module examples 10, 210, 310 shown in the figures are for purposes of illustration only, and any of various personality modules could be devised and incorporated in the system to accommodate any type or number of different catheters, physiological monitors, or other functional input types utilized in any cardiac laboratory procedure.

The dock 340 may include a computing system 50 with signal processing software capable of processing the physiological data prior to transmission to the base unit 60.

Referring also to FIG. 1, the computing system 50 of the dock 340 includes a processing system 51 having one or more processors capable of executing software stored in the storage system 52 comprised of one or more memory devices. The dock 340 may further include a power management module 54 that stores and provides power to the various elements within the dock 340, including the computing system 50 and/or the signal processing unit 42. Output from the computing system 50 is then provided through the transmission means 58 to the base unit 60. In other embodiments, the dock 340 may not include any computing system 50 and may just transmit the digitized physiological signals to the base unit 60 via the transmission means 58.

In certain embodiments, the dock 40, 240, 340 may be configured to receive two or more personality modules 10, 210, 310 simultaneously, such as to form an interface module 8 configured to receive two or more different catheter types or patient monitor types. FIG. 2B demonstrates an embodiment configured to receive four personality modules, and is configured to receive both active and passive personality modules and to provide a digital output to the base unit 60 of all received physiological signals. In the depicted embodiment, the dock 340 is receiving three different personality modules 210, 310a and 310b. The personality module 210 has a grid of 2 mm pin receivers 13 that provides an analog output to the dock 340, and thus is configured to receive any of various types of catheters having a ponytail connector. Also being connected to the dock 340 are two dedicated personality modules 310b and 310b, each having a respective dedicated catheter receiver 114a, 114b configured to receive a respective catheter type. The dedicated personality modules 310b and 310b each comprise specialized signal processing units 42 configured to process and digitized physiological data received from the respective catheter type.

In the example at FIG. 2B, the dock 40 is configured to receive four personality modules 10, but only three are being connected. The dock 40 may thus beneficially be configured with multi-modal connection ports 46 that are protected during periods of nonuse, such as to avoid introduction of fluid into the port. For example, each multi-modal connection port 46 may be recessed, and may include a plug or seal to close off the port when not in use.

Returning to FIG. 2A, the base unit 60 is configured to receive the analog or digital signals from the various interface modules 8. The base unit may comprise a computing system 62 having a communication interface 63 configured to receive the analog and/or digital physiological signals from the various interface modules 8 and transmit such signals to the processing system 64 for further processing, storage, and/or communication to the central review system 80. For example, the computing system 62 and the base unit 60 may comprise various software modules stored in the storage system 65 and configured to perform various signal processing tasks as required. The computing system 62 may also be configured to receive information about the status of various interface modules 8 and/or the physiological data acquisition devices 3, 6 connected thereto, such as information identifying those devices and/or identifying whether the connected devices are on and/or functioning properly. Thus, the base unit 60 may include a user interface 67 on the housing 61 for conveying such information. The user interface 67 may be very simple, such as that depicted in FIG. 2A comprising a power button 91 on the housing 61 configured to turn on the base unit 60 and various indicator lights 92 and 93 on the housing 61 configured to indicate whether the connected devices are on and transmitting physiological signals or data to the base unit 60. For example, active indicator lights 92 may be provided to indicate whether the base unit 60 is receiving analog or digital physiological signals from various interface modules. An error light 93 may be configured to indicate when an error is detected in one of the interface modules.

The base unit 60 may further be configured to acquire any number of different physiological parameters from the patient, such as blood pressure, heart rate, respiratory data, blood oxygen saturation level, etc. Such information may be provided by directly connecting physiological monitors to the base unit 60. In the example, the base unit 60 includes an ECG receiver port 95 and multiple pressure receiver ports 97 for connection to an ECG monitor and multiple blood pressure monitors, respectively. In various embodiments, the blood pressure monitors may be noninvasive blood pressure monitors (NIBP) or invasive blood pressure monitors (IBP), or a combination of both types of monitors. While such dedicated physiological recording inputs are available, as explained above, those same physiological parameters may also be received through one or more interface modules 8 having personality modules 10 configured to receive the electrode connections or other physiological recording inputs.

The base unit 60 is then configured to communicate the physiological data to the central review system 80, which displays the acquired information to the clinician and facilitates storage of the acquired information in a database, such as in the patient's medical record and/or the procedure record. For example, the central review system 80 may incorporate Mac-Lab, ComboLab, CardioLab, and/or Centricity Cardiology products (or their successors) by General Electric Company of Schenectady, New York. The central review system 80 includes one or more computing systems 82, which may be part of a computer network at a healthcare facility and/or a cloud-hosted computing network. The central review system may include one or more user interfaces 87 through which a clinician can receive and review the physiological data recorded by all of the various physiological data acquisition devices 3, 6 and/or provide instructions for controlling the system 1.

FIGS. 3-7 provide various examples of docks 40 and corresponding personality modules 10, which are configured to mate together in order to form a customized interface module 8. To facilitate secure connection between the dock 40 and the personality module 10, each has a correspondingly shaped housing such that the dock 40 and personality module 10 are mountable with respect to one another and mate together in order to form an interface module 8 that is compact, stable, and transportable. The dock 40 has a dock housing 41 and the personality module has a personality module housing 11, where each are correspondingly shaped to facilitate connection of the housings together. It will be understood by a person having ordinary skill in the art that the figures provide non-limiting examples of connection and mounting means between the dock housing 41 and the personality module housing 11, and that the dock housing 41 and the personality module housing 11 may have any corresponding connection means that enable mating the two housings together. In certain embodiments, the housings 11 and 41 may be provided with corresponding locking means to lock the housings together in the mated position. For example, one of the housings 11, 41 may have a locking detent (such as a spring-mounted piece) that engages a notch or other corresponding portion of the housing of the other housing 41, 11. In such an embodiment, the locking detent may be released by depressing the detent or a connected button or portion to disengage the lock and allow separation of the personality module 10 and the dock 40. Thereby, if the detent is not released then the personality module 10 remains secured to the dock 40.

Figure 3A:
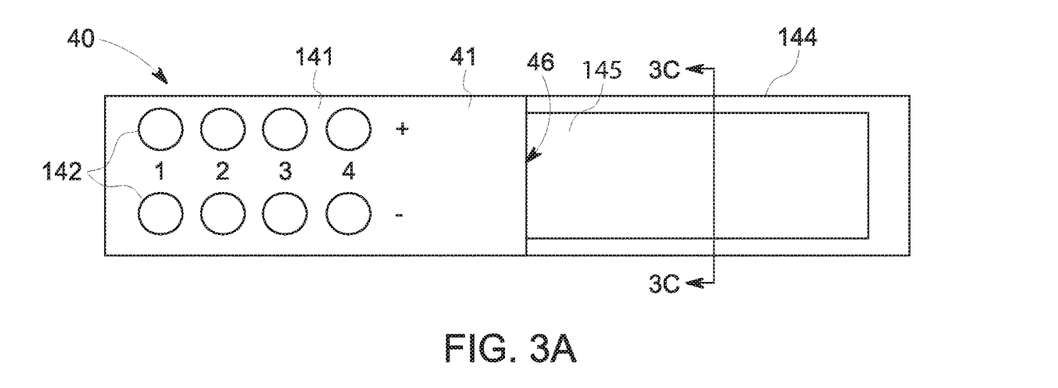
FIGS. 3A-3C depict an exemplary embodiment of a dock comprising part of an interface module according to the present disclosure.
Figure 3B:
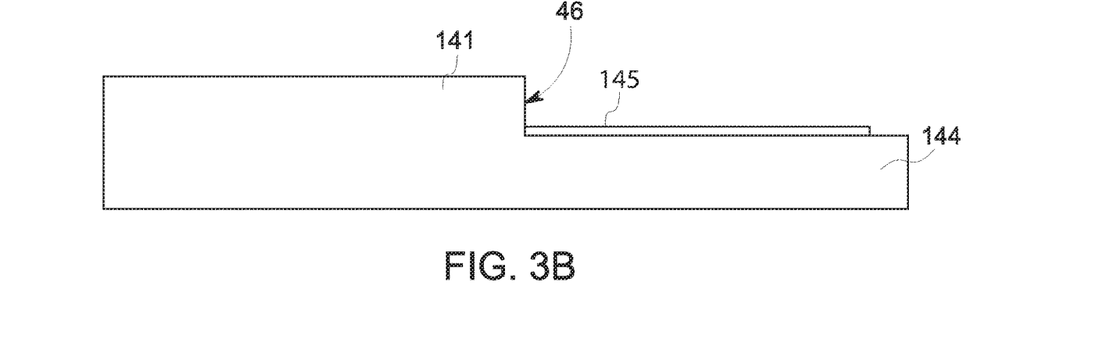
Figure 3C:
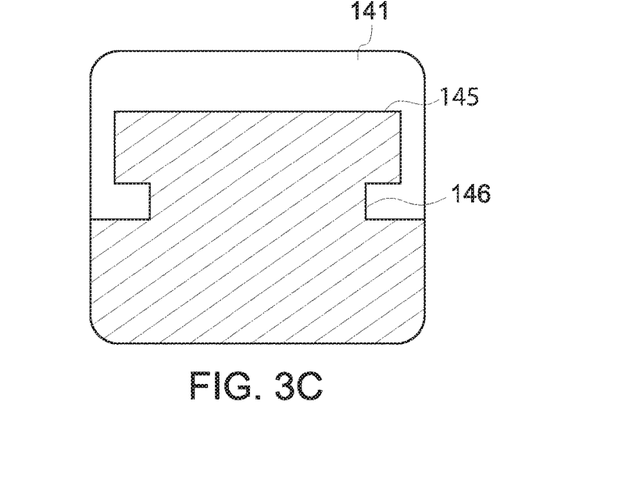
Figure 4A:
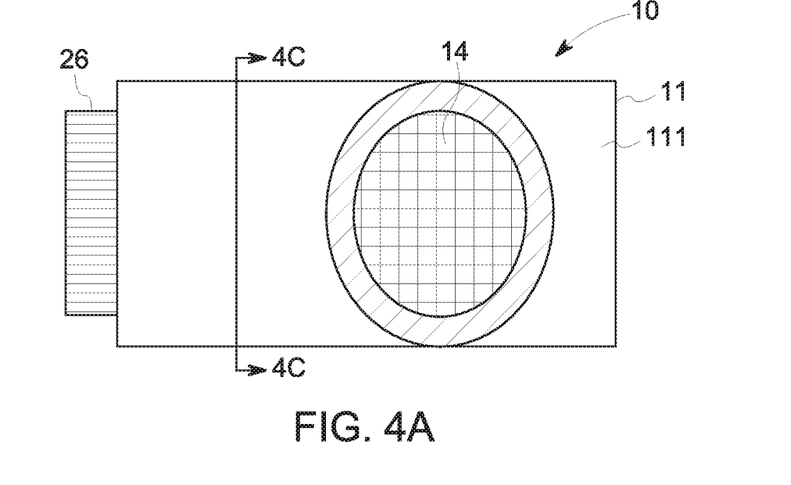
FIGS. 4A-4C depict one embodiment of a personality module configured to mate with the dock in FIGS. 3A-3C to form an interface module according to one embodiment of the present disclosure.
Figure 4B:
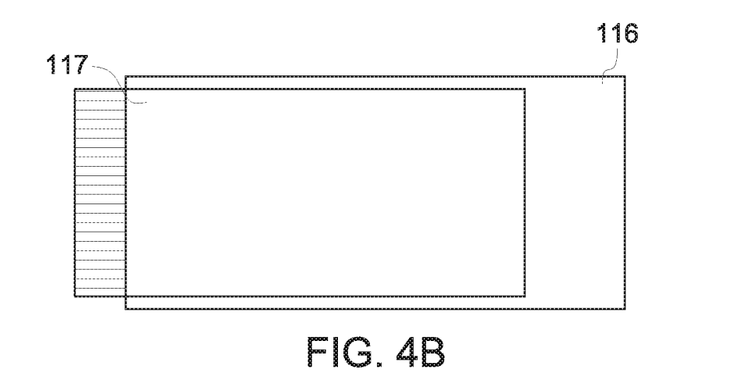
Figure 4C:
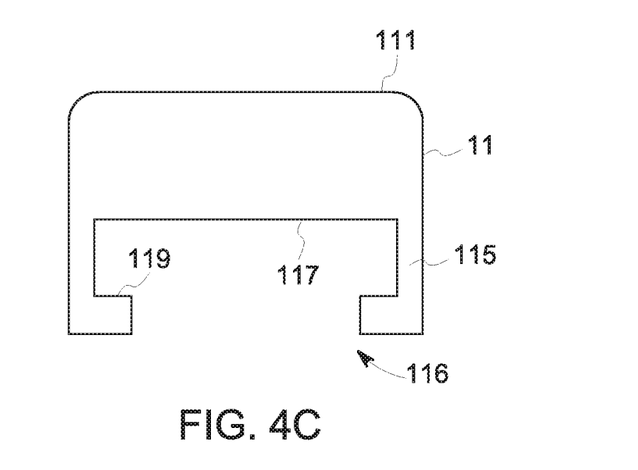

FIGS. 3A-3C provide one exemplary dock housing 41 having connection means for connecting with the correspondingly shaped personality module 10 shown in FIGS. 4A-4C. FIG. 3A is a top view, FIG. 3B is a side view, and FIG. 3C is a cross-sectional view of the exemplary of the dock housing 41 embodiment. FIG. 4A is a top view, FIG. 4B is a bottom view, and FIG. 4C is a cross sectional view of the corresponding personality module housing 11. In this example, the dock 40 and the personality module 10 slidably connect together in order to insert the dock connector 26 of the personality module 10 into the multi-modal connection port 46 of the dock 40. The dock housing 41 has a platform portion 144 and a main body portion 141. The platform portion 144 is configured to receive and support the personality module 10. In this example, the platform 144 has a raised section 145 having tracks 146 on either side thereof for slidably engaging the personality module housing 11. Specifically, the bottom side 116 of the personality module housing 11 has a recessed portion 117 configured to receive the raised section 145 of the dock housing 41. The personality module housing 11 further has legs 115 that terminate in a lip 119 that wraps around the raised section 145 and engages the track 146 of the dock housing 41. The personality module 10 slides onto the dock 40 such that the dock connector 26 connects to the multi-modal connection port 46. Once connected, the dock housing 41 and the personality module housing 11 are securely mated together such that the interface module 8 can be transported without the personality module 10 inadvertently separating from the dock 40. Thereby, a customized interface module 8 is provided.

A top surface 111 of the personality module housing 11 provides the one or more catheter or patient monitor receivers 12. In the depicted example, a top surface of the dock housing 41 provides emergency stimulator connectors 142, which provide the ability to utilize catheters placed in the patient as emergency pacemakers in the event of total failure of the system 1. The emergency stimulator connectors 142 provide for direct electrical connection to the STIM input(s) 103 provided on the base unit 60. In certain embodiments, the dock 40 may further provide one or more auxiliary reference inputs (not shown) allowing a clinician to build an analog channel without using a catheter and bypassing the interface module 8. For example, a reference electrode may be provided on the patient, such as a patch on the back or the leg of the patient, and plugged into an auxiliary reference input in the dock 40. Alternatively, such a reference electrode may be connected directly to the auxiliary input 104 on the base unit 60.

Figure 5A:
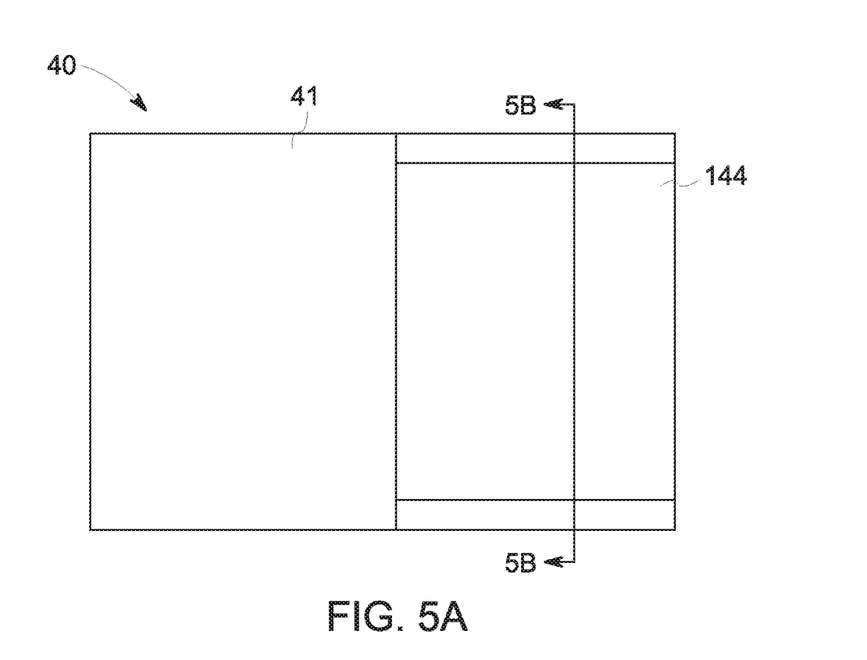
FIGS. 5A-5B depict another embodiment of a dock according to the present disclosure.
Figure 5B:
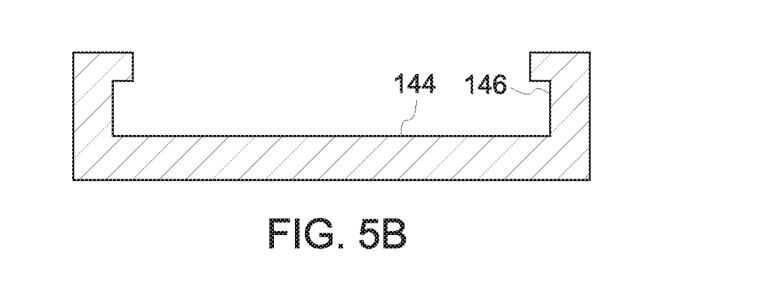
Figure 6A:
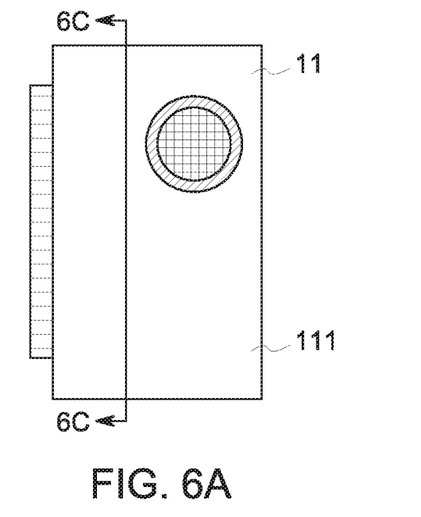
FIGS. 6A-6C depict one embodiment of a personality module configured to mate with the dock depicted in FIGS. 5A and 5B.
Figure 6B:
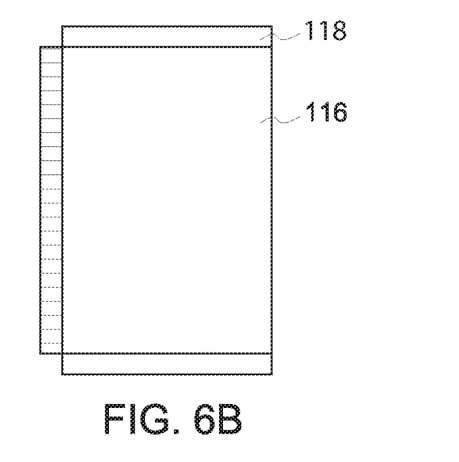
Figure 6C:
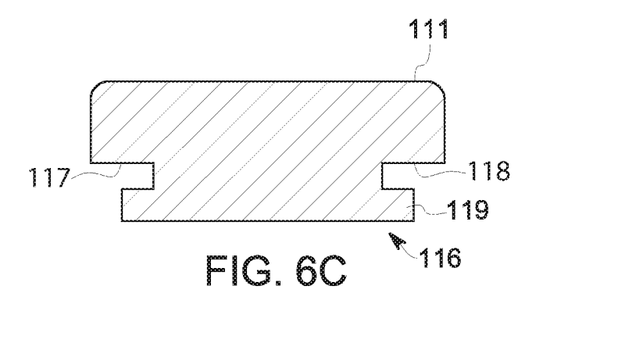

FIGS. 5A-5B and 6A-6C depict another embodiment of correspondingly shaped dock housing 41 and personality module housing 11 that slidably connect together. As shown in FIGS. 5A and 5B, the dock housing 41 has a platform 144 with tracks 146 that extend upward from the platform 144. The correspondingly shaped personality module housing 11 has a bottom side 116 with recessed edges 118 that are shaped to receive the tracks 146 that protrude from the platform 144 of the dock housing 41. The personality module housing 41 has a lip 119 on either side that extends outward to engage an underside of the track 146.

Figure 7A:
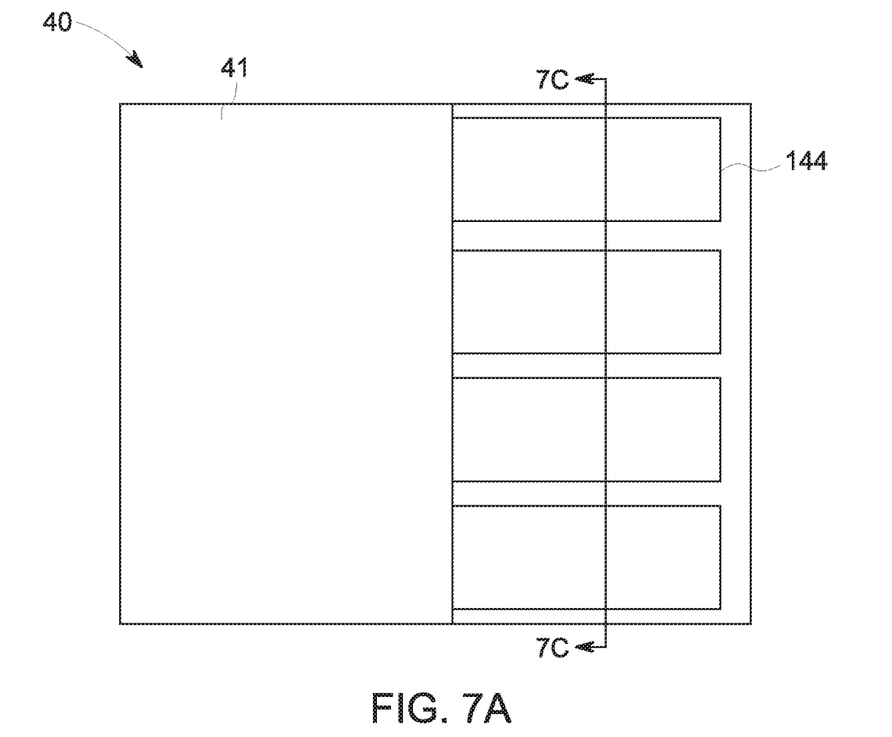
FIGS. 7A-7C depict another embodiment of a dock according to the present disclosure, wherein the dock is configured to receive four personality modules.
Figure 7B:
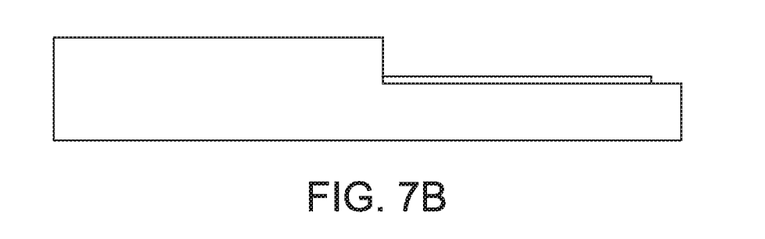
Figure 7C:
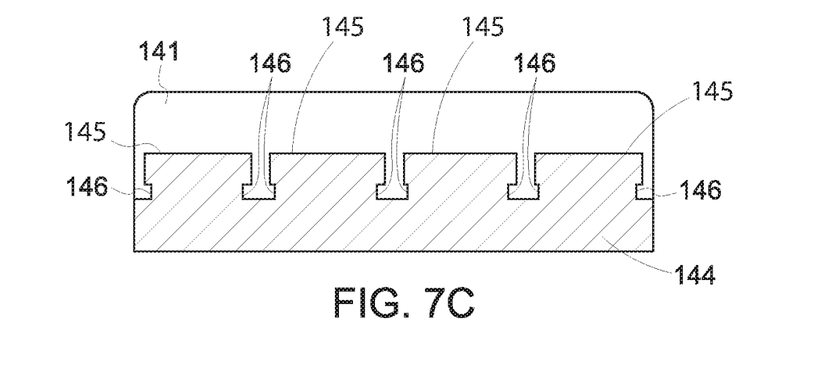

FIGS. 7A-7C depict an exemplary embodiment of a dock 40 having a dock housing 41 configured to slidably mate with multiple personality modules. The platform 144 is configured with multiple raised sections 145 having tracks 146 on either side that each slidably engage a personality module 10. In various embodiments, the tracks 146 may be arranged differently than is shown here, such as one track centered under each personality module housing 11, instead of two tracks, one along either bottom edge of the personality module 10. In still other embodiments, the personality module housing 11 and the dock housing 41 may engage one another by other connection means, such as any clip, clasp, pressure fit, or friction connection. For example, the dock housing 41 may comprise one or more spring loaded clasps or clips configured to engage the lip 119 or other protrusion or indentation in the personality module housing 11.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A physiological data acquisition system comprising:
   at least two interface modules, wherein each interface module comprises:
      a dock configured to mate with two or more different personality modules, the dock including a dock housing with a multi-modal connection port thereon and configured to directly connect to a dock connector of any one of the two or more different personality modules so as to receive physiological signals therefrom, the dock including a processor configured to process at least a portion of the physiological signals received from the connected personality module;
      a connected one of the two or more different personality modules including:
         a personality module housing;
         a catheter receiver configured to removably receive a connection end of the catheter so as to receive physiological signals therefrom;
         a dock connector on the personality module housing configured to connect to the multi-modal connection port of the dock so as to provide the physiological signals thereto in a communication sent from the connected one of the personality modules to the dock;
      wherein each dock housing and each personality module housing mate together to form each interface module; and
   a base unit configured to communicatively connect to the at least two interface modules to receive the physiological signals therefrom, and wherein the processor is configured to communicate with the base unit.

2. The physiological data acquisition system of claim 1, wherein each dock housing and each personality module housing are correspondingly shaped such that they mate together to form the interface module.

3. The physiological data acquisition system of claim 1, wherein a first one of the two or more different personality modules comprises a first catheter receiver that is a dedicated catheter receiver configured to receive the connection end of a first catheter type, wherein the first catheter type is one of a fixed curve catheter, a mapping catheter, a steerable catheter, an ablation catheter, and a multi-array catheter.

4. The physiological data acquisition system of claim 3, further comprising at least a second personality module configured to mate with each dock of the at least two interface modules, the second personality module including a second catheter receiver configured to receive a connection end of a second catheter type so as to receive physiological measurement signals therefrom, wherein the second catheter type is a different one of the fixed curve catheter, the mapping catheter, the steerable catheter, an ablation catheter, or a multi-array catheter than the first catheter type.

5. The physiological data acquisition system of claim 4, wherein the dock of at least one of the at least two interface modules is configured to receive only one personality module at a time, and to interchangeably receive either one of the first or second personality modules.

6. The physiological data acquisition system of claim 4, wherein the dock of at least one of the at least two interface modules is configured to simultaneously mate with the first personality module and the second personality module and further includes transmission means configured to transmit the physiological signals received from both the first catheter type and the second catheter type to the base unit.

7. The physiological data acquisition system of claim 3, wherein the first personality module comprises a signal processing unit configured to process signals from the first catheter type; and
wherein the signal processing unit digitizes the physiological signals to generate processed physiological data, wherein the first personality module provides the processed physiological data to the dock.

8. The physiological data acquisition system of claim 3, wherein the first personality module comprises a signal processing unit configured to process signals from the first catheter type, wherein the signal processing unit filters the physiological signals from the first catheter type to produced filtered analog signals.

9. The physiological data acquisition system of claim 8, wherein the personality module provides the filtered analog signals; and
wherein the dock of at least one of the at least two interface modules further comprises a signal processing unit configured to digitize the filtered analog signals from the first catheter type to generate processed physiological data, wherein the dock provides the processed physiological data to the base unit.

10. The physiological data acquisition system of claim 3, further comprising at least a second personality module configured to mate with the dock of at least one of the at least two interface modules, the second personality module including a physiological monitor receiver configured to receive a connection end of one or more physiological sensors so as to receive physiological measurement signals therefrom, wherein the sensors include EEG electrodes or an invasive blood pressure sensor.

11. The physiological data acquisition system of claim 1, wherein the dock housing of each dock of each of the at least two interface modules comprises a platform configured to mate with the personality module housing of any one of the two or more different personality modules.

12. The physiological data acquisition system of claim 11, wherein each dock housing further comprises a track on or adjacent to the platform, wherein the track is configured to slidably engage a lip on the personality module housing of any one of the two or more different personality modules.

13. The physiological data acquisition system of claim 11, wherein the platform is configured to mate with housings of at least two of the two or more different personality modules.

14. The physiological data acquisition system of claim 1, wherein the dock of at least one of the at least two interface modules comprises at least one emergency stimulator connector configured to connect to a stimulation catheter to provide stimulation.

15. A physiological data acquisition system comprising:
a plurality of personality modules, each personality module including:
a personality module housing;
a catheter receiver on the personality module housing, the catheter receiver configured to removably receive a connection end of a catheter type so as to receive physiological signals therefrom;
a dock connector on the personality module housing, the dock connector configured to connect to a multi-modal connection port of a dock so as to provide the physiological signals thereto;
a first interface module comprising:
a first dock configured to mate with at least one of the plurality of personality modules, the first dock including:
a first dock housing;
a first multi-modal connection port on the first dock housing configured to connect to at least a first personality module of the plurality of personality modules so as to receive physiological signals therefrom;
a first dock computing system configured to communicate with the first personality module;
wherein the first dock housing and the first personality module housing are correspondingly shaped such that they mate together to form the first interface module;
a second interface module comprising:
a second dock configured to mate with at least one of the plurality of personality modules, the second dock including:
a second dock housing;
a second multi-modal connection port on the second dock housing configured to connect to at least a second personality module of the plurality of personality modules so as to receive physiological signals therefrom;
a second dock computing system configured to communicate with the second personality module;
wherein the second dock housing and the second personality module housing are correspondingly shaped such that they mate together to form the second interface module;
a base unit configured to communicatively connect to the first interface module and the second interface module to receive the physiological signals therefrom; and
wherein the first dock computing system and the second dock computing system are configured to communicate with the base unit.

16. The physiological data acquisition system of claim 15, wherein the first and second multi-modal connection ports on the first and second docks are identical such that both the first dock and the second dock are configured to interchangeably receive either one of the first and the second personality modules.

17. The physiological data acquisition system of claim 15, further comprising at least a third personality module including:
- a third personality module housing that is correspondingly shaped with the first and second dock housings such it can interchangeably mate therewith to form the first interface module or the second interface module; and
- a physiological monitor connector on the third personality module housing, the physiological monitor connector configured to receive a connection end of one or more sensors so as to receive physiological signals therefrom.

* * * * *